(12) United States Patent
Colleran et al.

(10) Patent No.: US 6,656,183 B2
(45) Date of Patent: Dec. 2, 2003

(54) TISSUE REPAIR SYSTEM

(75) Inventors: Dennis Colleran, North Attleborough, MA (US); Stefan Gabriel, Mattapoisett, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 09/986,376

(22) Filed: Nov. 8, 2001

(65) Prior Publication Data

US 2003/0088250 A1 May 8, 2003

(51) Int. Cl.[7] ............................................... A61B 17/56
(52) U.S. Cl. ........................................ 606/72; 606/232
(58) Field of Search ..................... 606/72, 232, 75, 606/60, 139

(56) References Cited

U.S. PATENT DOCUMENTS

| | | | |
|---|---|---|---|
| 4,532,926 A | 8/1985 | O'Holla |
| 4,548,202 A | 10/1985 | Duncan |
| 4,632,100 A | 12/1986 | Somers et al. |
| 4,946,468 A | 8/1990 | Li |
| 5,002,550 A | 3/1991 | Li |
| 5,013,316 A | 5/1991 | Goble et al. |
| 5,037,422 A | 8/1991 | Hayhurst et al. |
| 5,041,129 A | 8/1991 | Hayhurst et al. |
| 5,100,417 A | 3/1992 | Cerier et al. |
| 5,152,790 A | 10/1992 | Rosenberg et al. |
| 5,156,616 A | 10/1992 | Meadows et al. |
| 5,192,303 A | 3/1993 | Gatturna et al. |
| 5,224,946 A | 7/1993 | Hayhurst et al. |
| 5,236,445 A | 8/1993 | Hayhurst et al. |
| 5,261,914 A | 11/1993 | Warren |
| 5,282,809 A | 2/1994 | Kammerer et al. |
| 5,324,308 A | 6/1994 | Pierce |
| 5,330,491 A | 7/1994 | Walker et al. |
| 5,336,240 A | 8/1994 | Metzler et al. |
| 5,354,298 A | 10/1994 | Lee et al. |
| 5,370,662 A | 12/1994 | Stone et al. |
| 5,372,604 A | 12/1994 | Trott |
| 5,391,173 A | * 2/1995 | Wilk .......................... 606/232 |
| 5,403,348 A | 4/1995 | Bonutti |
| 5,411,523 A | 5/1995 | Goble |
| 5,417,691 A | 5/1995 | Hayhurst |
| 5,423,860 A | 6/1995 | Lizardi et al. |
| 5,464,427 A | 11/1995 | Curtis et al. |
| 5,472,452 A | 12/1995 | Trott |
| 5,480,403 A | 1/1996 | Lee et al. |
| 5,486,197 A | 1/1996 | Le et al. |
| 5,501,683 A | 3/1996 | Trott |

(List continued on next page.)

FOREIGN PATENT DOCUMENTS

| | | |
|---|---|---|
| EP | 0464480 | 1/1992 |
| EP | 0502509 A1 | 9/1992 |
| EP | 0574707 | 12/1993 |
| WO | 92/04874 | 4/1992 |
| WO | 95/29637 | 11/1995 |

*Primary Examiner*—Kevin T. Truong
(74) *Attorney, Agent, or Firm*—Fish & Richardson P.C.

(57) ABSTRACT

A bone anchor includes an anchor body configured to be retained within bone. The anchor body includes a restrictor defining an opening having a first portion for permitting passage of a member therethrough, and a second portion restricting passage of the member therethrough. The member is movable between the first and second portions in a direction non-parallel to a direction of passage of the member through the opening. The restrictor includes an edge lining the opening oriented obliquely to a direction of passage of the member through the opening. The anchor body includes one or more resilient members with sharp, proximal edges for penetrating bone tissue.

32 Claims, 12 Drawing Sheets

U.S. PATENT DOCUMENTS

| | | |
|---|---|---|
| 5,522,843 A | 6/1996 | Zang |
| 5,522,844 A | 6/1996 | Johnson |
| 5,522,846 A | 6/1996 | Bonutti |
| 5,536,273 A | 7/1996 | Lehrer |
| 5,545,180 A | 8/1996 | Le et al. |
| 5,554,171 A | 9/1996 | Gatturna et al. |
| 5,569,306 A | 10/1996 | Thal |
| 5,578,057 A | 11/1996 | Wenstrom, Jr. |
| 5,584,835 A | 12/1996 | Greenfield |
| 5,584,860 A | 12/1996 | Goble et al. |
| 5,591,177 A | 1/1997 | Lehrer |
| 5,601,557 A | 2/1997 | Hayhurst |
| 5,609,597 A | 3/1997 | Lehrer |
| 5,630,824 A | 5/1997 | Hart |
| 5,643,320 A | 7/1997 | Lower et al. |
| 5,645,589 A | 7/1997 | Li |
| 5,647,874 A | 7/1997 | Hayhurst |
| 5,658,313 A | 8/1997 | Thal |
| 5,665,112 A | 9/1997 | Thal |
| 5,669,935 A | 9/1997 | Rosenman et al. |
| 5,683,419 A | 11/1997 | Thal |
| 5,690,676 A | 11/1997 | DiPoto et al. |
| 5,702,397 A * | 12/1997 | Goble et al. ............... 606/72 |
| 5,709,708 A | 1/1998 | Thal |
| 5,720,765 A | 2/1998 | Thal |
| 5,720,766 A | 2/1998 | Zang et al. |
| 5,725,529 A | 3/1998 | Nicholson et al. |
| 5,725,557 A | 3/1998 | Gatturna et al. |
| 5,728,136 A | 3/1998 | Thal |
| 5,735,875 A | 4/1998 | Bonutti et al. |
| 5,741,300 A | 4/1998 | Li |
| 5,782,862 A | 7/1998 | Bonutti |
| 5,782,864 A | 7/1998 | Lizardi |
| 5,782,866 A * | 7/1998 | Wenstrom, Jr. ............ 606/232 |
| 5,814,051 A | 9/1998 | Wenstrom, Jr. |
| 5,824,011 A | 10/1998 | Stone et al. |
| 5,827,291 A | 10/1998 | Fucci et al. |
| 5,843,087 A | 12/1998 | Jensen et al. |
| 5,885,294 A | 3/1999 | Pedlick et al. |
| 5,891,168 A | 4/1999 | Thal |
| 5,893,592 A | 4/1999 | Schulze et al. |
| 5,897,564 A | 4/1999 | Schulze et al. |
| 5,897,574 A | 4/1999 | Bonutti |
| 5,904,696 A | 5/1999 | Rosenman |
| 5,906,624 A | 5/1999 | Wenstrom, Jr. |
| 5,911,721 A | 6/1999 | Nicholson et al. |
| RE36,289 E | 8/1999 | Le et al. |
| 5,941,882 A | 8/1999 | Jammet et al. |
| 5,944,724 A | 8/1999 | Lizardi |
| 5,944,739 A | 8/1999 | Zlock et al. |
| 5,948,002 A | 9/1999 | Bonutti |
| 5,961,538 A | 10/1999 | Pedlick et al. |
| 5,968,044 A | 10/1999 | Nicholson et al. |
| 5,980,557 A | 11/1999 | Iserin et al. |
| 5,980,558 A | 11/1999 | Wiley |
| 5,993,459 A | 11/1999 | Larsen et al. |
| 6,007,566 A | 12/1999 | Wenstrom, Jr. |
| 6,022,373 A * | 2/2000 | Li ............... 606/232 |
| 6,024,758 A | 2/2000 | Thal |
| 6,027,523 A | 2/2000 | Schmieding |
| 6,036,701 A | 3/2000 | Rosenman |
| 6,045,573 A | 4/2000 | Wenstrom, Jr. et al. |
| 6,045,574 A | 4/2000 | Thal |
| 6,066,160 A * | 5/2000 | Colvin et al. ............... 606/232 |
| 6,146,406 A | 11/2000 | Shluzas et al. |
| 6,149,669 A * | 11/2000 | Li ............... 606/232 |
| 6,179,840 B1 | 1/2001 | Bowman |
| 6,306,159 B1 | 10/2001 | Schwartz |
| 6,355,066 B1 * | 3/2002 | Kim ............... 606/232 |

* cited by examiner

TISSUE REPAIR SYSTEM

BACKGROUND

This invention relates to tissue fixation devices and methods for tissue repair.

Fibrous tissues, such as ligaments and tendons, can detach from bone. The detachment can be repaired using sutures. It is known to fix a fibrous tissue to bone by inserting a suture anchor through the fibrous tissue and into the bone and knotting suture attached to the anchor to tie down the fibrous tissue to the bone. Tying suture knots in minimally invasive surgical procedures commonly requires a skilled surgeon and/or specialized equipment.

SUMMARY

According to one aspect of the invention, a bone anchor includes an anchor body configured to be retained within bone and to selectively restrict movement of a flexible member coupled to the bone anchor such that after implantation, the flexible member can be moved through the anchor body in a first direction while, without the aid of an enlarged portion on the flexible member, e.g., a knot, movement in a second, opposite direction can be restricted.

Embodiments of this aspect of the invention may include one or more of the following features. The bone anchor includes a restrictor configured to engage the flexible member to selectively restrict movement of the flexible member. The restrictor is configured to engage the flexible member at a substantially arbitrary position along a length of the flexible member. The anchor body defines an opening through which the flexible member can be moved, and the restrictor is configured to engage the flexible member to selectively restrict passage of the flexible member through the opening. The restrictor defines at least a part of the opening, for example, a narrower portion of the opening than another portion of the opening.

In an illustrated embodiment, the restrictor includes a sloped surface configured to compress the flexible member to permit passage of the flexible member through the opening, and opposing edges for engaging the flexible member to limit passage of the flexible member through the opening.

The bone anchor includes a second restrictor configured to engage the flexible member to selectively restrict passage of the flexible member through the opening. The restrictors are oppositely directed.

The anchor body includes a pair of legs, a bone-engaging ridge for retaining the bone anchor in a bone hole, and a post about which the flexible member is positionable. The anchor body is a unitary body.

According to another aspect of the invention, a tissue repair system includes a first anchor body including a member that engages bone to retain the anchor within the bone and a second anchor body including a member that engages bone to retain the anchor within the bone. The anchor bodies each define an opening for receiving suture and a restrictor forming a one-way passage through the opening. The anchor bodies are coupled by a suture extending through the one-way passages.

According to another aspect of the invention, a bone anchor includes an anchor body configured to be retained within bone and to receive a flexible member such that after implantation of the anchor body within bone, the flexible member can be moved through the anchor body while, without the aid of an enlarged portion on the flexible member, subsequent movement of the anchor body can be restricted.

According to another aspect of the invention, a tissue repair system includes a flexible member, and first and second bone anchors coupled together by the flexible member. Each bone anchor includes an anchor body configured to be retained within bone. At least one of the bone anchors is configured to receive the flexible member such that the flexible member can be pulled to shorten a length of the flexible member between the bone anchors, while, without the aid of an enlarged portion on the flexible member, subsequent lengthening of the flexible member between the bone anchors can be restricted.

According to another aspect of the invention, a bone anchor includes an anchor body configured to be retained within bone. The anchor body defines a one-way passage configured to pass a suture in a first direction and restrict passage of the suture in a second direction opposite the first direction.

According to another aspect of the invention, a bone anchor includes an anchor body configured to be retained within bone. The anchor body includes a restrictor defining an opening having a first portion for permitting passage of a member therethrough, and a second portion restricting passage of the member therethrough without the aid of an enlarged portion on the member.

According to another aspect of the invention, a method includes placing an anchor in bone, moving a flexible member through the anchor in a first direction, and restricting movement of the flexible member through the anchor in a second, opposite direction.

Embodiments of this aspect of the invention may include placing a second anchor in bone. The second anchor is coupled to the first anchor by the flexible member. The step of moving the flexible member in the first direction shortens a length of the flexible member between the anchors.

According to another aspect of the invention, a bone anchor includes an anchor body configured to be retained within bone. The anchor body includes a restrictor defining an opening having a first portion for permitting passage of a member therethrough, and a second portion restricting passage of the member therethrough. The member is movable between the first and second portions in a direction non-parallel to a direction of passage of the member through the opening.

Embodiments of this aspect of the invention may include one or more of the following features.

The restrictor includes one or more edges lining a wall of the opening. The edge is oriented obliquely to a direction of passage of the member through the opening. Some of the edges are oriented at the same oblique angle relative to the direction of passage of the member through the opening, and some of the edges are oriented parallel to each other.

A dimension of the second portion is narrower than a diameter of the member. The opening is triangular in shape. The anchor is configured such that the member is movable between the first and second portions substantially perpendicularly to a direction of passage of the member through the opening.

In an illustrated embodiment, the anchor body includes a tissue penetrating tip, and a central body member with a driver coupling. The anchor body includes one or more resilient members with sharp, proximal edges for penetrating bone tissue. The anchor body is a unitary body.

According to another aspect of the invention, a tissue repair system includes a first bone anchor with an anchor body configured to be retained within bone, and a second bone anchor with an anchor body configured to be retained within bone. A flexible member couples the first and second bone anchors. At least one of the first and second anchor bodies includes a restrictor defining an opening having a first portion for passage of the flexible member therethrough, and a second portion limiting passage of the flexible member therethrough. The flexible member is movable between the first and second portions in a direction non-parallel to a direction of passage of the member through the opening.

According to another aspect of the invention, a bone anchor includes an anchor body configured to be retained within bone. The anchor body includes a restrictor defining an opening for passage of a member therethrough. The restrictor includes an edge lining a wall of the opening oriented such that upon movement of the member through the opening in a first direction, the member is also moved non-parallel to the first direction.

Embodiments of this aspect of the invention may include the edge being oriented such that upon movement of the member through the opening in a second direction opposite the first direction, the member is also moved non-parallel to the second direction. The restrictor includes a second edge lining a wall of the opening. The second edge is oriented such that upon movement of the member through the opening in a second direction opposite the first direction, the member is also moved non-parallel to the second direction.

According to another aspect of the invention, a method includes placing an anchor in bone and moving a member between first and second portions of an opening in the anchor in a direction non-parallel to a direction of passage of the member through the opening.

Embodiments of this aspect of the invention may include one or more of the following features.

The method includes engaging the member with an edge lining the opening. Moving the member to the second portion includes moving the member in a direction substantially perpendicular to a direction moved by the member through the first portion. A second anchor coupled to the first anchor by the member is placed in the bone.

Advantages of the invention may include permitting surgeons with varying skill levels to straightforwardly reattach tissue to bone in open or closed surgical procedures. The surgeon is able to fix a fibrous tissue to bone using an appropriate tension simply by pulling a suture received by the bone anchor in a first direction. Since the bone anchors of the present invention limit subsequent movement of the suture in the opposite direction, the surgeon is able to easily select the appropriate tension.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
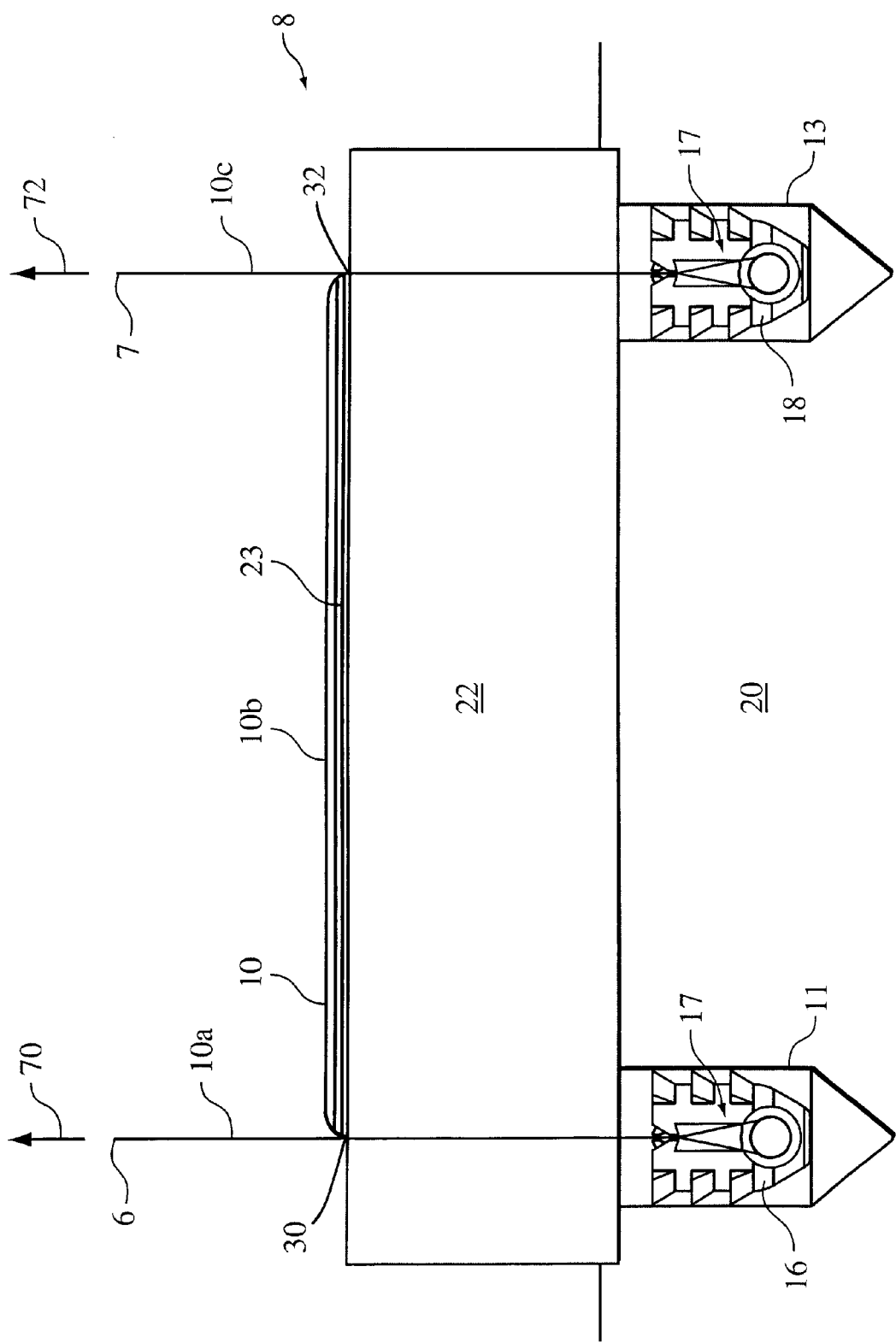
FIG. 1 is a diagrammatic illustration of a system for reattaching fibrous tissue to bone.

Referring to FIG. 1, a tissue repair system 8 for attaching soft tissue 22, e.g., tendon, ligament, or cartilage, to bone 20 includes a flexible member, e.g., suture 10, coupled to first and second bone anchors 16, 18. Suture 10 includes contiguous suture portions 10a, 10b and 10c. In use, bone anchors 16, 18 are located within holes 11, 13 in bone 20, with first suture portion 10a extending from bone anchor 16 through a hole 30 in tissue 22 to a first suture end 6, second suture portion 10b spanning between bone anchors 16, 18 and lying along an outer surface 23 of tissue 22, and third suture portion 10c extending from bone anchor 18 through a hole 32 in tissue 22 to a second suture end 7.

Bone anchors 16, 18 each include a first engagement system 17 through which suture 10 is threaded. After implantation in bone 20, the physician pulls on one or both of the ends 6, 7 of suture 10 to shorten the length of suture portion 10b, thus securing tissue 22 against bone 20. Engagement systems 17, discussed further below, couple suture 10 to bone anchors 16, 18 and limit possible loosening of tissue repair system 8 following tissue securement.

Figure 2A:
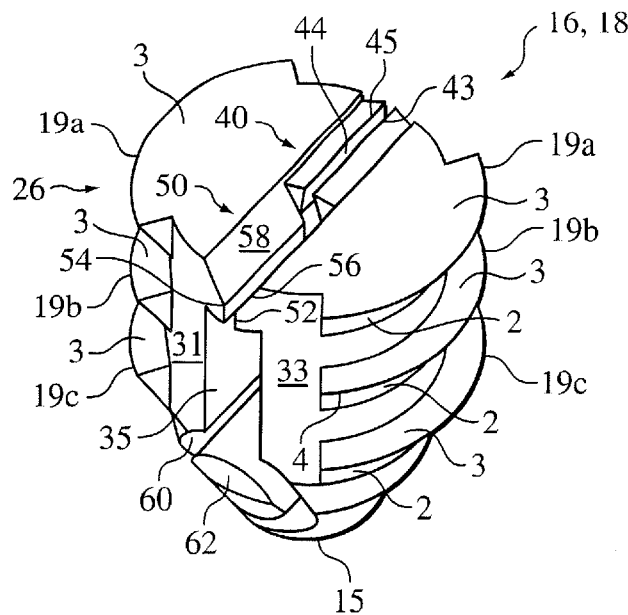
FIG. 2A is a perspective view of a bone anchor.
Figure 2C:
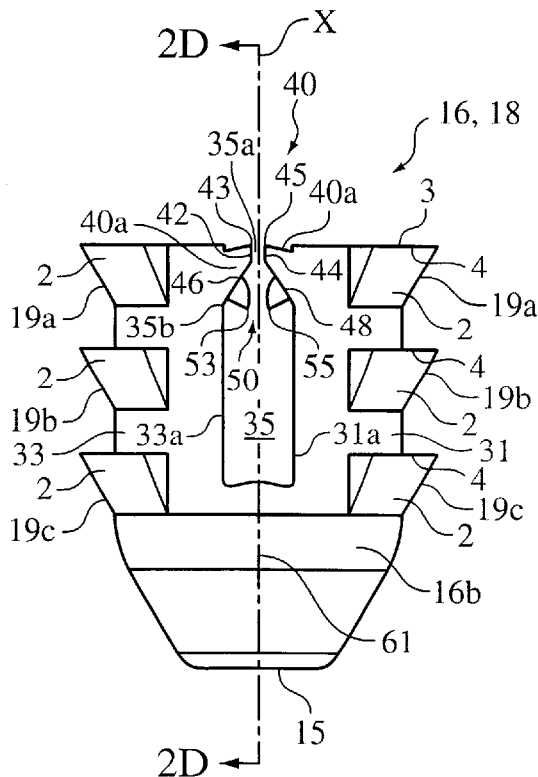
FIGS. 2B and 2C are side views of the bone anchor of FIG. 2A.

Referring to FIG. 2A, bone anchors 16, 18 each have a flat, distal tip 15 and a pair of legs 31, 33 extending proximally from tip 15 to a proximal end 26. Legs 31, 33 are generally part-circular in shape (FIG. 2E) with a region of increased outer diameter defined by a series of radial ridges (here three ridges 19a, 19b, 19c shown) that engage bone tissue to resist the withdrawal of the anchor from the bone hole. Each ridge 19a, 19b, 19c has a sloped distal face 2, a proximal face 3 that is substantially normal to the long axis, X, of bone anchors 16, 18, and a bone engaging edge 4 (FIG. 2B) defined at the intersection of faces 2 and 3.

Engagement system 17 includes a pair of restrictor cleats 40, 50 at the proximal end 26 of legs 31, 33. Legs 31, 33 have inner walls 31a, 33a (FIG. 2B), respectively, that define a slot opening 35 therebetween extending from proximal end 26 to a distal chamber 60. Located within chamber 60 is a winding post 62. The open sides of slot opening 35 provide easy access to winding post 62 to aid in threading suture 10 around post 62, though the sides need not be open. Cleats 40, 50 act to selectively restrict passage of suture 10 through opening 35, as described further below.

Figure 2D:
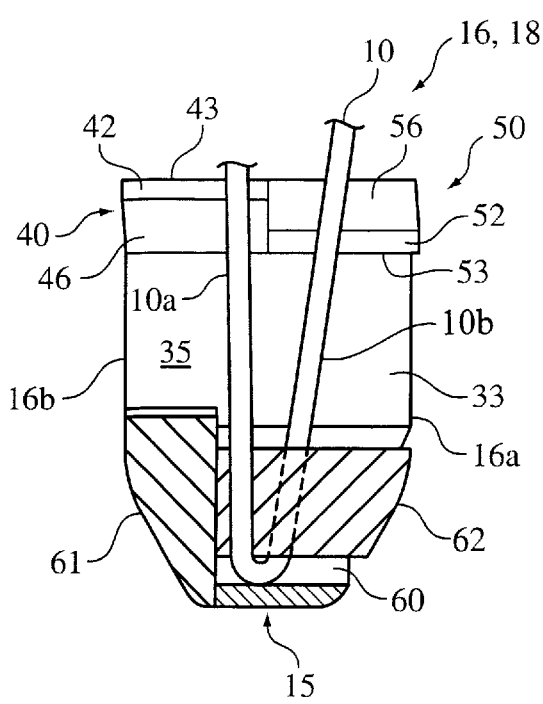
FIG. 2D is a cross-sectional view of the bone anchor of FIG. 2A taken along lines 2D—2D of FIGS. 2B and 2C.
Figure 2E:
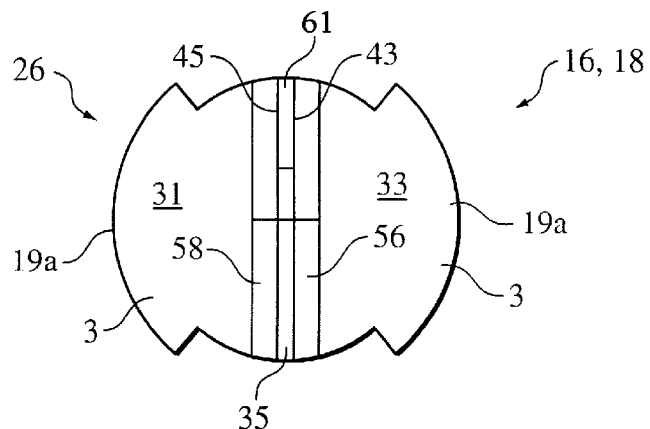
FIGS. 2E and 2F are respectively top and bottom views of the bone anchor of FIG. 2A.

As shown in FIG. 2D, winding post 62 extends into chamber 60 from a wall 61 at a back side 16b of anchor 16. Winding post 62 and wall 61 are tapered inwardly toward distal tip 15 to provide a smooth, tapered distal portion. Chamber 60 circumscribes winding post 62, and is open at a front side 16a of the bone anchor to aid in threading suture 10 through anchor 16. Suture 10 is threaded through anchor 16 such that the suture passes through cleat 50 and opening 35, into interior chamber 60 and around winding post 62, then through opening 35 and cleat 40. Winding post 62 contacts and retains suture 10 within interior chamber 60, and is of sufficient mechanical strength to withstand tension applied to suture 10.

Figure 2B:
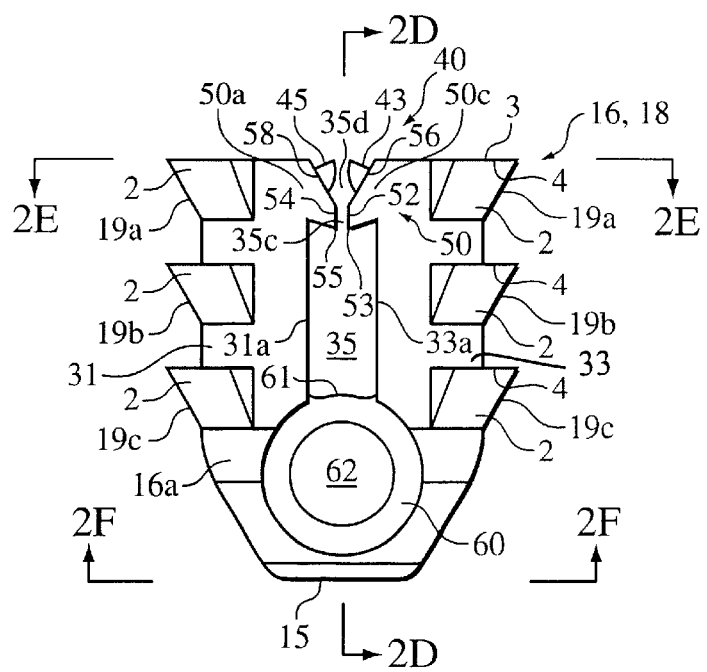
Figure 2F:
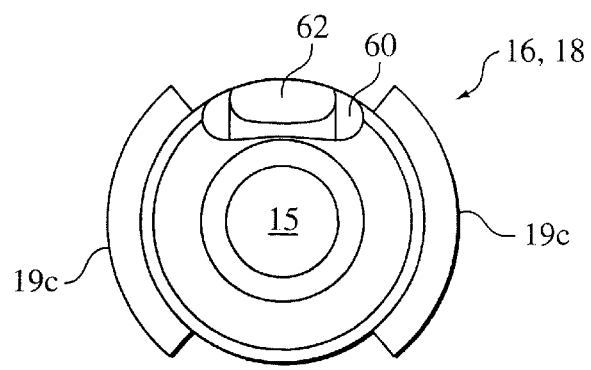

Referring to FIGS. 2B and 2C, cleat 40 is formed by an opposing pair of protrusions 40a having proximal faces 42, 44 that define a narrower portion 35a of channel 35 therebetween, and distal faces 46, 48 that define a wider, sloped portion 35b of channel 35 therebetween. Cleat 50 is oriented opposite of cleat 40 with an opposing pair of protrusions 50a having distal faces 52, 54 that define a narrower portion 35c of channel 35 therebetween, and proximal faces 56, 58 that define a wider, sloped portion 35d of channel 35 therebetween. Proximal faces 42, 44 have opposing edges 43, 45 (defined by the proximal corners of faces 42, 44), and distal faces 52, 54 have opposing edges 53, 55 (defined by the distal corners of faces 52, 54). Each opposing pair of edges 43, 45 and 53, 55 is separated by a separation distance that is substantially equal to or smaller than the diameter of suture 10.

Movement of suture 10 through sloped portions 35b, 35d of cleats 40, 50 acts to compress the suture such that the suture can pass through narrower portions 35a, 35c, respectively, when pulled in the direction of arrow 70 (FIG. 1). However, loosening of suture 10 (passage of suture 10 through the cleats in a direction opposite arrow 70) is limited by opposing edges 43, 45 and 53, 55 catching on uncompressed suture 10 such that the suture does not pass through the cleats. In effect, cleats 40, 50 form a one-way passage.

Referring again to FIG. 1, suture 10 is threaded through anchors 16 and 18 such that from suture end 6, suture portion 10a passes through cleat 40 in anchor 16 to post 62, suture portion 10b extends from post 62 through cleat 50 in anchor 16, then through cleat 50 in anchor 18, to post 62, and suture portion 10c extends from post 62 through cleat 40 in anchor 18 to suture end 7. This permits the suture to pass through the cleats (with the sloped portions of the cleats compressing the suture such that the suture can pass through the narrow portions of the cleats) when ends 6, 7 are pulled in the directions of arrows 70, 72, respectively, to shorten suture length 10b, but resists passage through the cleats (by the opposing edges of the cleats catching on uncompressed suture) when a load tending to lengthen suture length 10b is placed on the suture.

In use, the operator implants first and second bone anchors 16, 18 into, e.g., a predrilled hole in bone 20 through tissue 22 (and an overlaying cartilage layer, if present) by, e.g., applying a compressive or torsional load to members 16, 18 as appropriate. The operator then draws one or both ends 6, 7 of suture portions 10a, 10c in the direction of arrows 70, 72 to shorten the length of suture portion 10b between first and second bone anchors 16, 18. Suture portion 10b draws tissue 22 toward bone 20. The anchors can be supplied to the operator with suture 10 prethreaded to through anchors 16, 18, or the operator can thread suture 10 through the anchors.

When suture portion 10b is sufficiently taut, the operator releases and/or cuts the free ends of the suture extending from the soft tissue. Although, during healing, a patient may apply forces that tend to draw tissue 22 away from bone 20, engagement systems 17 resist the lengthening of suture portion 10b. In particular, cleats 40, 50 restrict passage of the suture portion 10c in the direction opposite to arrow 72 and suture portion 10a in the direction opposite to arrow 70. Moreover, cleats 40, 50 engage and restrict the passage of suture 10 at a substantially arbitrary position along the length of suture 10. In other words, there is no need, e.g., to clamp suture 10 with another member, or have an enlarged portion such as a knot in suture 10 to restrict the passage of suture 10 through the cleats. Cleats 40, 50 thus selectively restricts movement of suture 10 by allowing the passage of suture 10 through the cleats in a first direction while subsequent passage of suture 10 in a second, opposite direction is restricted.

Figure 3A:
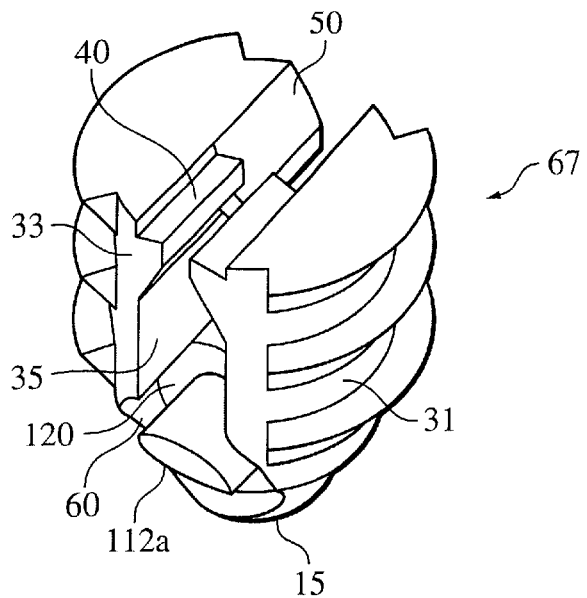
FIG. 3A is a perspective view of an alternative embodiment of a bone anchor.
Figure 3B:
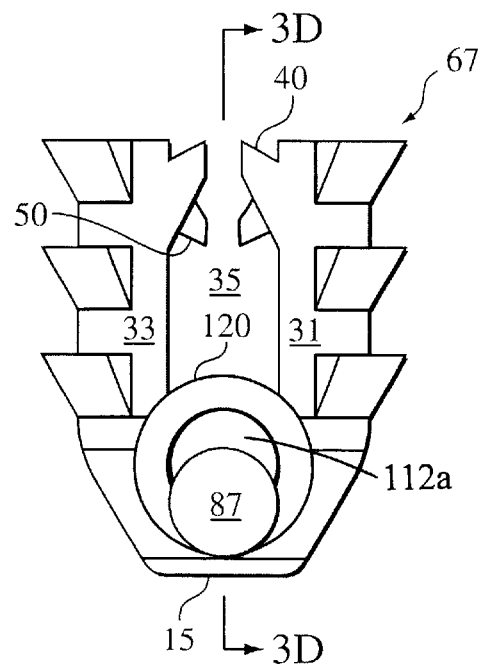
FIGS. 3B and 3C are side views of the bone anchor of FIG. 3A.
Figure 3D:
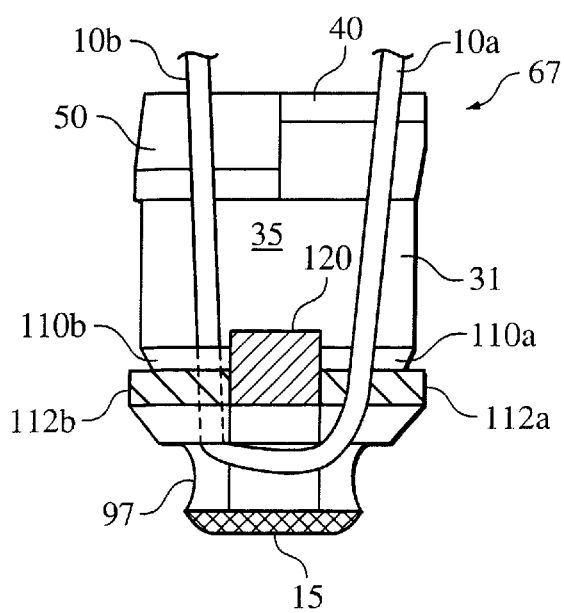
FIG. 3D is a cross-sectional view of the bone anchor of FIG. 3A taken along lines 3D—3D of FIGS. 3B and 3C.
Figure 3E:
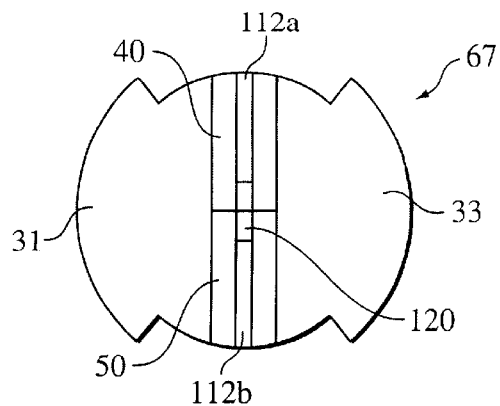
FIGS. 3E and 3F are respectively top and bottom views of the of the bone anchor of FIG. 3A.
Figure 3C:
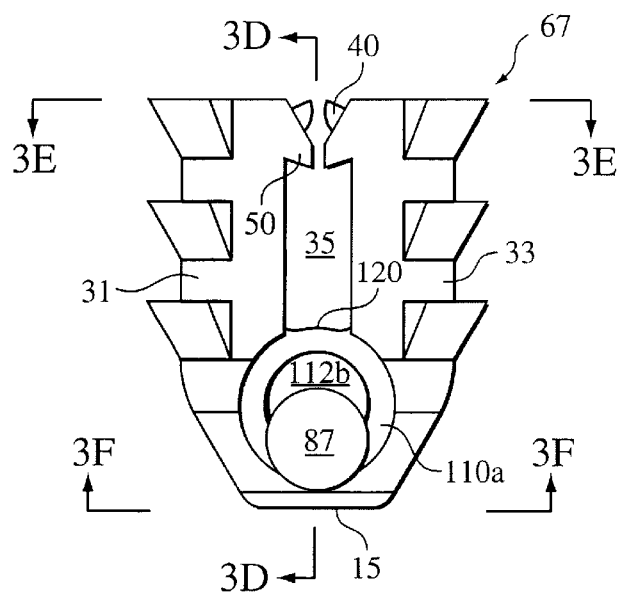
Figure 3F:
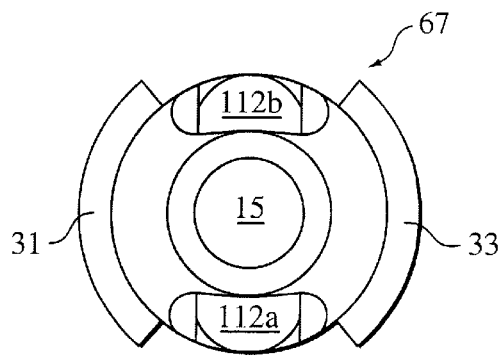
Figure 3G:
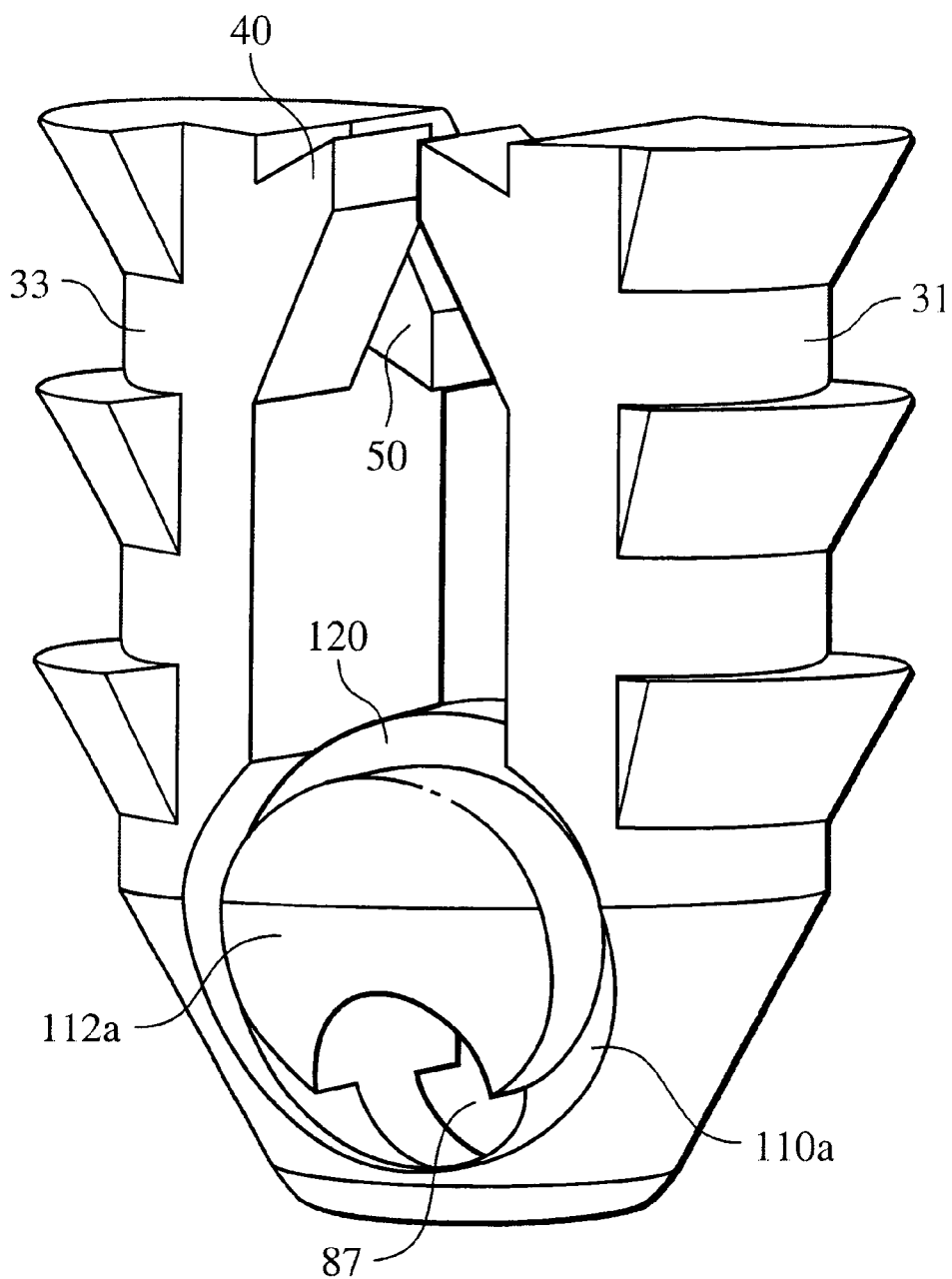
FIG. 3G is another perspective view of the bone anchor of FIG. 3A.

Other embodiments are within the scope of the following claims. For example, referring to FIGS. 3A–3F, particularly to FIGS. 3A and 3D, rather than a post 62 extending from a side wall, an alternate bone anchor 67 includes a central member 120 with side posts 112a, 112b located in chamber 60. Side posts 112a, 112b taper inwardly to provide a smooth, tapered distal portion. The outer dimension of side posts 112a, 112b is less than the diameter of chamber 60 such that channels 110a, 110b, respectively, are formed about side posts 112a, 112b, while the outer diameter of central member 120 is equal to the diameter of chamber 60. Posts 112a, 112b and central member 120 defines a transverse passage 87 (FIG. 3G) for passage of suture from channel 110a to 110b. Side posts 112a, 112b have a half-moon shape such that a circular suture passage 87 is formed. Other side posts shapes are possible. Suture 10 passes through cleat 40 to channel 35, to channel 110a and around post 112a to passage 87, through passage 87, to channel 110b around post 112b to channel 35, and through cleat 50.

Figure 4A:
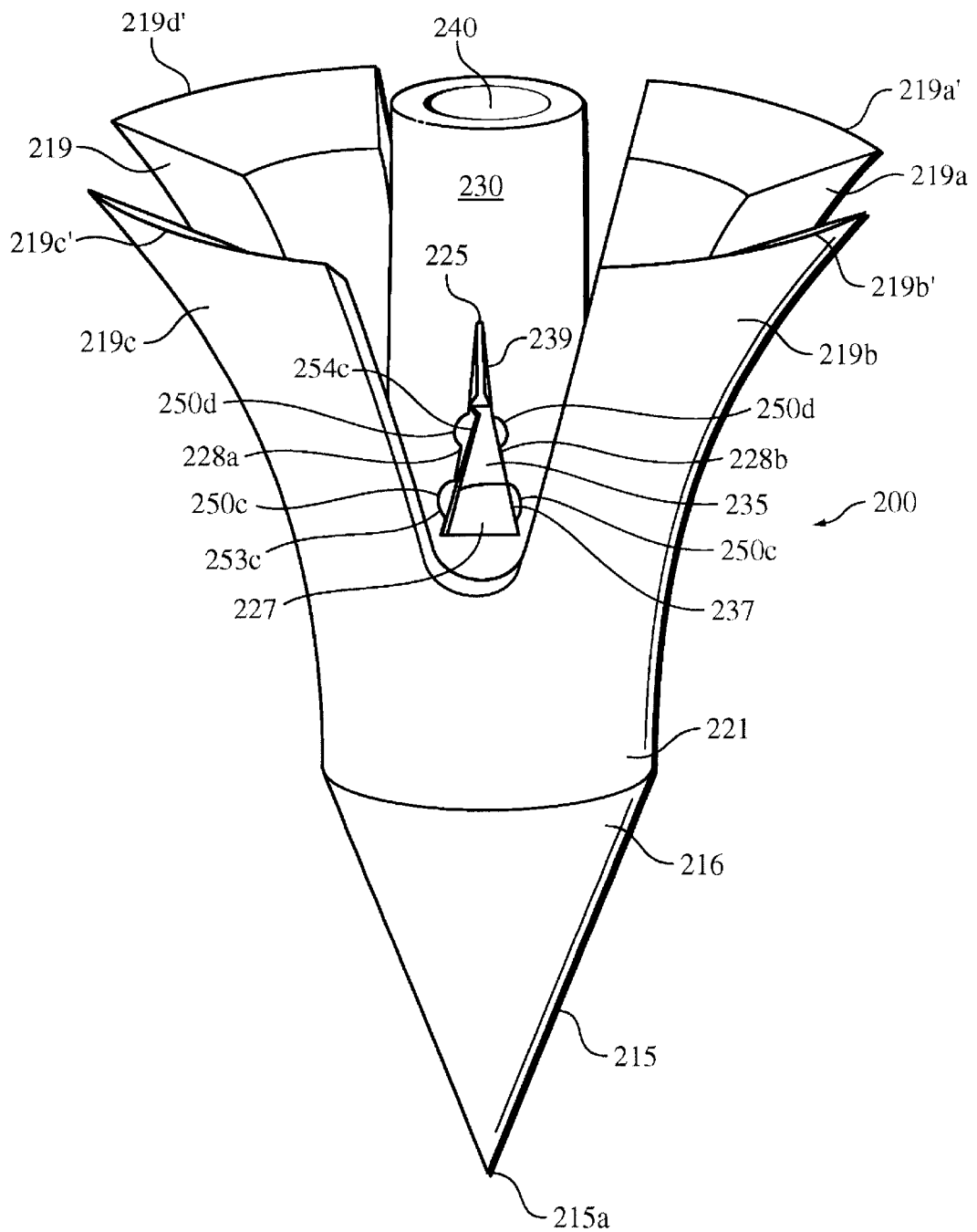
FIG. 4A is a perspective view of another alternative embodiment of a bone anchor.

Referring to FIG. 4A, a bone anchor 200 includes a central member 230, a distal tip 215, and a series of proximally extending, radial wings 219a, 219b, 219c, 219d surrounding central member 230. Central member 230 includes a restrictor in the form of a suture guiding through channel 235 that selectively restricts passage of suture therethrough, as described below. Distal tip 215 is conical in shape and has a tissue penetrating point 215a. Radial wings 219a, 219b, 219c, 219d are joined at a distal end 221 of the wings to a proximal end 216 of distal tip 215, and resiliently flare outwardly from central member 230 in a proximal direction. Each wing has a sharp proximal edge 219a', 219b', 219c', 219d' for digging into bone tissue to resist withdrawal of anchor 200 from the bone. Wings 219a, 219b, 219c, 219d are inwardly deformable toward central member 230 in response to radial compression, such as during insertion into a generally circular opening or hole in bone formed, e.g., by insertion of distal tip 215 into the bone. Central member 230 defines a proximal opening 240 for receiving a drive tool, not shown, for pounding anchor 200 into bone.

Figure 4C:
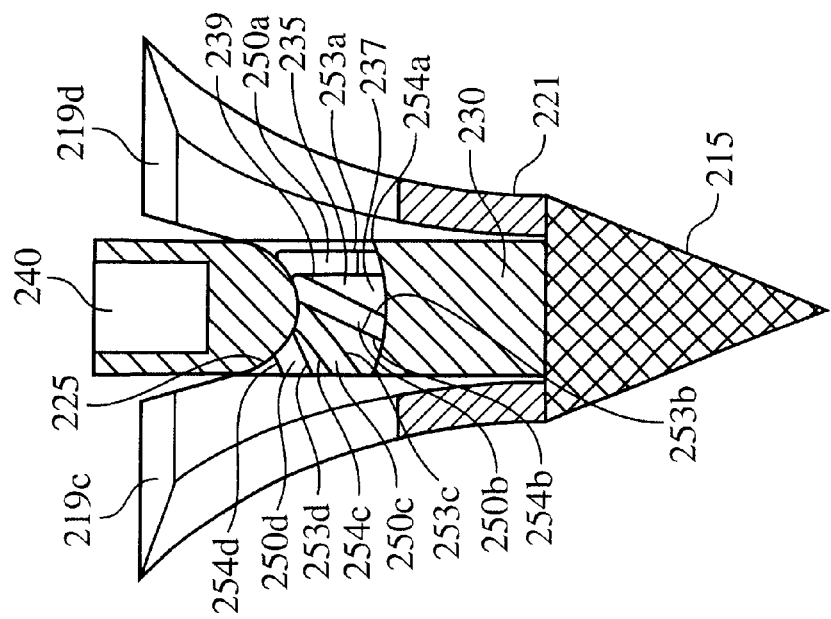
FIG. 4C is a cross-sectional side view of the bone anchor of FIG. 4A taken along lines 4C—4C of FIG. 4B.
Figure 4B:
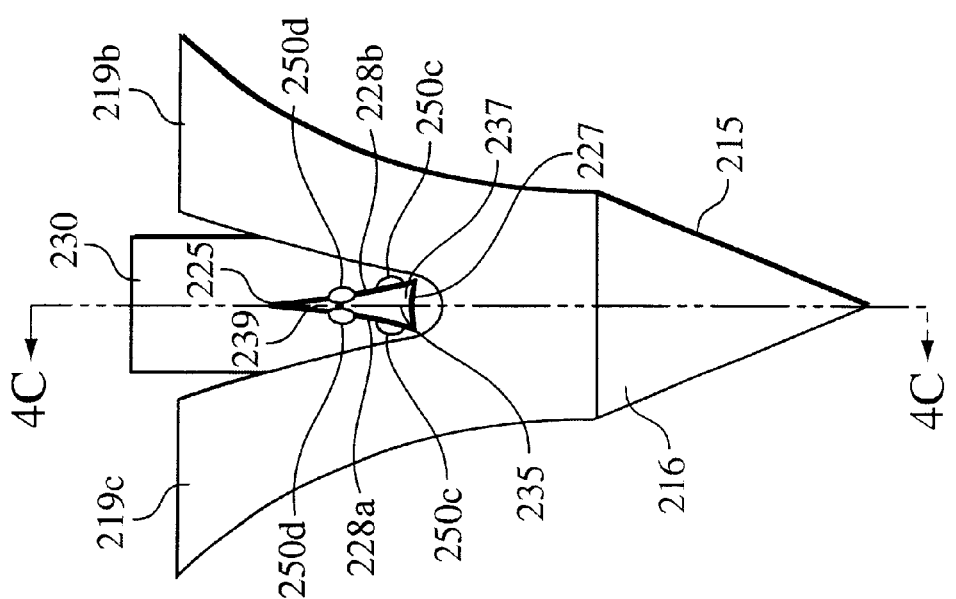
FIG. 4B is a side view of the bone anchor of FIG. 4A.
Figures 4D, 4E:
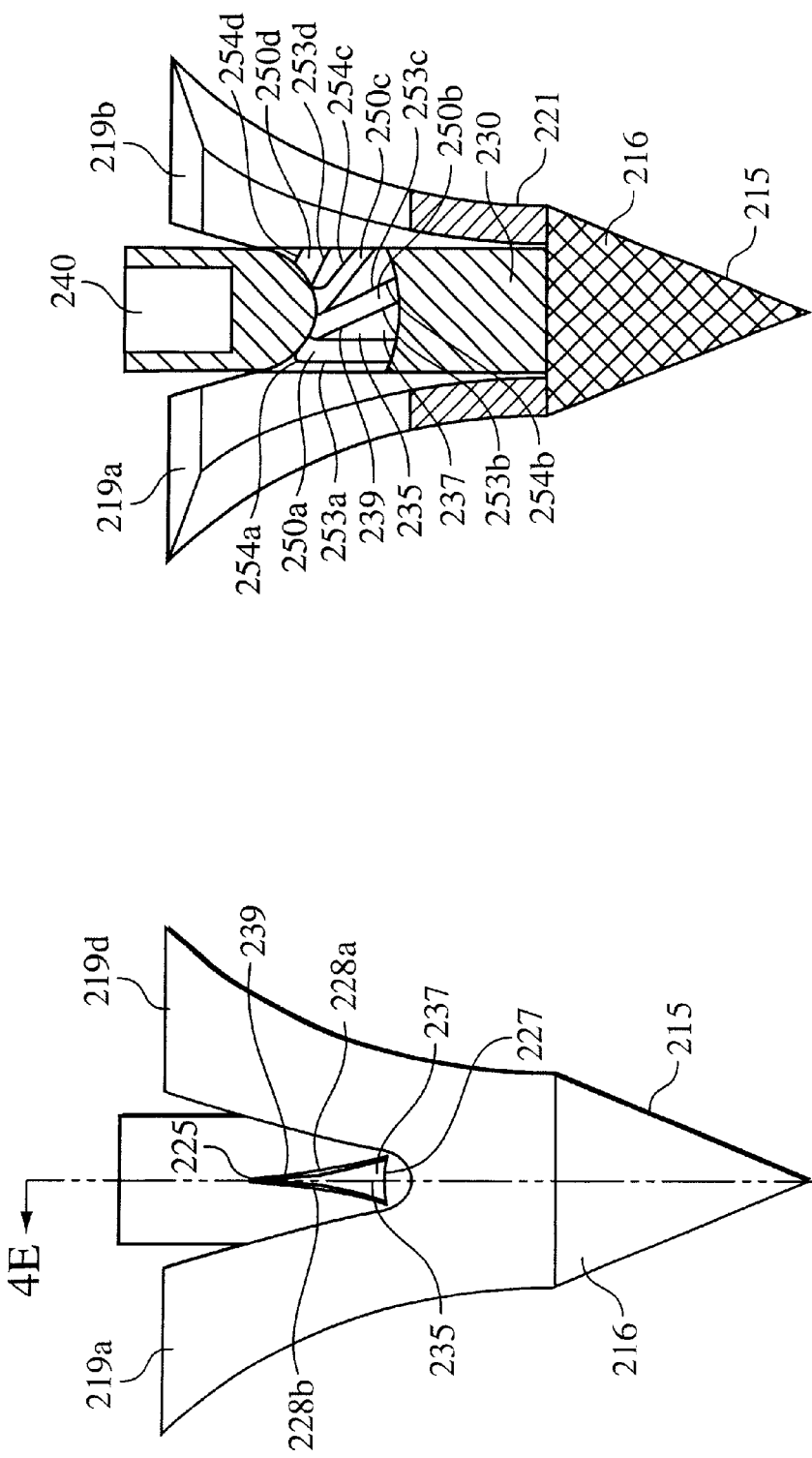
FIG. 4D is another side view of the bone anchor of FIG. 4A.
FIG. 4E is a cross-sectional side view of the bone anchor of FIG. 4A taken along lines 4E—4E of FIG. 4D.
Figure 4G:
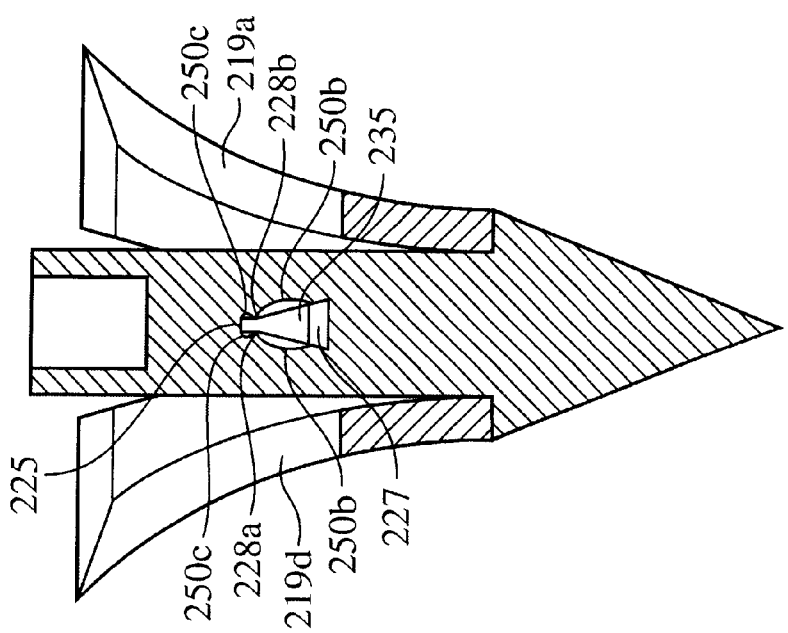
FIG. 4G is a cross-sectional side view of the bone anchor of FIG. 4A taken along lines 4G—4G of FIG. 4F.
Figure 4F:
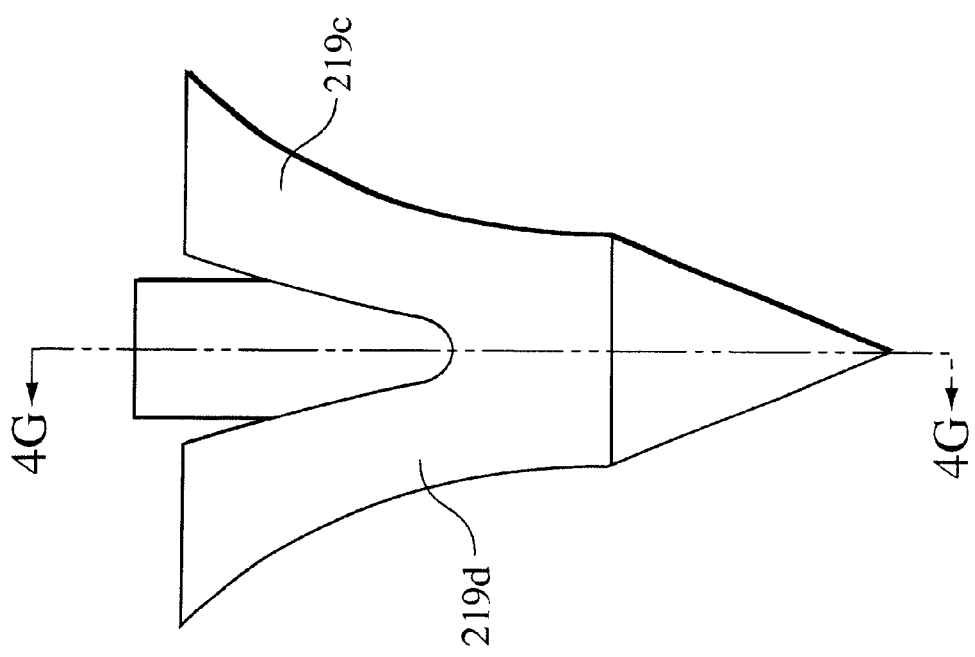
FIG. 4F is another side view of the bone anchor of FIG. 4A.

Referring to FIGS. 4B–4G, suture guiding channel 235 has a generally triangular cross-section with a proximal apex 225, a distal base face 227, and a pair of side faces 228a, 228b. Side faces 228a, 228b converge proximally forming a distal portion 237 of channel 235 that is wider than the diameter of the suture, such that the suture can pass freely therethrough, and a proximal restricting portion 239 of channel 235 that is narrower than the suture diameter to restrict passage of the suture therethrough. Referring particularly to FIGS. 4C and 4E, base face 227 follows an arcuate path through central member 230, as does apex 225 at the intersection of side faces 228a, 228b. As illustrated, the radius of curvature of the path of apex 225 though central member 230 is approximately equal to one half the diameter of central member 230. The curvature of apex 225 presents an atraumatic surface for the suture to rest against when pulled taught, as discussed below.

Figure 5:
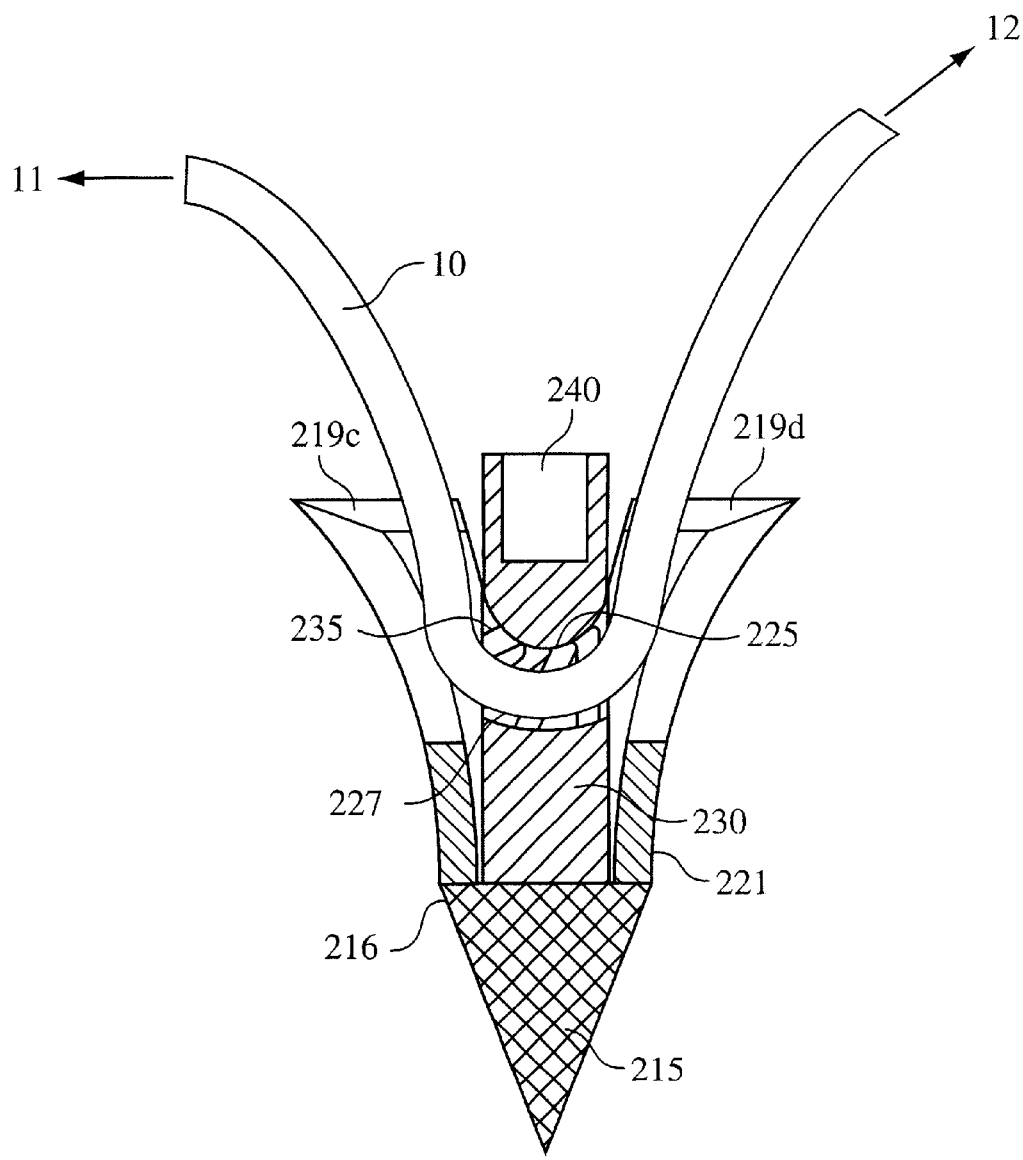
FIG. 5 is a cross-sectional side view of the bone anchor of FIG. 4A shown with a suture coupled thereto.

Side faces 228a, 228b are each lined by a series of grooves 250a, 250b, 250c, 250d. Though four grooves are shown, one or more grooves can be employed. As illustrated, grooves 250a, 250b, 250c, 250d are relatively uniformly oriented with respect to base face 237 and apex 225 of channel 235 such that the grooves have the same oblique angle relative to a suture passing through channel 235, as shown in FIG. 5. Each groove 250a–250d has a first edge 253a–253d, respectively, and a second edge 254a–254d, respectively, oriented generally parallel to the respective first edge and obliquely relative to the passage of suture 10 through channel 235.

Edges 253a–253d and 254a–254d, along with the shape of channel 235, act to permit suture to be pulled in a first direction while limiting movement of the suture in a second opposite direction. Referring to FIGS. 4C and 5A, when suture 10 is pulled in the direction of arrow 11, contact of suture 10 with edges 253a–253d pushes suture 10 in a direction non-parallel to the direction of travel of suture 10 through channel 235. The action of edges 253a–253d upon suture 10 moves suture 10 toward base face 227 into distal channel portion 237, allowing suture 10 to pass through channel 235. When suture 10 is pulled in the direction of arrow 12, contact of suture 10 with edges 254a–254d pushes suture 10 in a direction non-parallel to the direction of travel of suture 10 through channel 235. The action of edges 254a–254d upon suture 10 moves suture 10 toward apex 225 into proximal restricting portion 239, which acts to compress suture 10 and restrict passage of suture 10 through channel 235.

Figure 6:
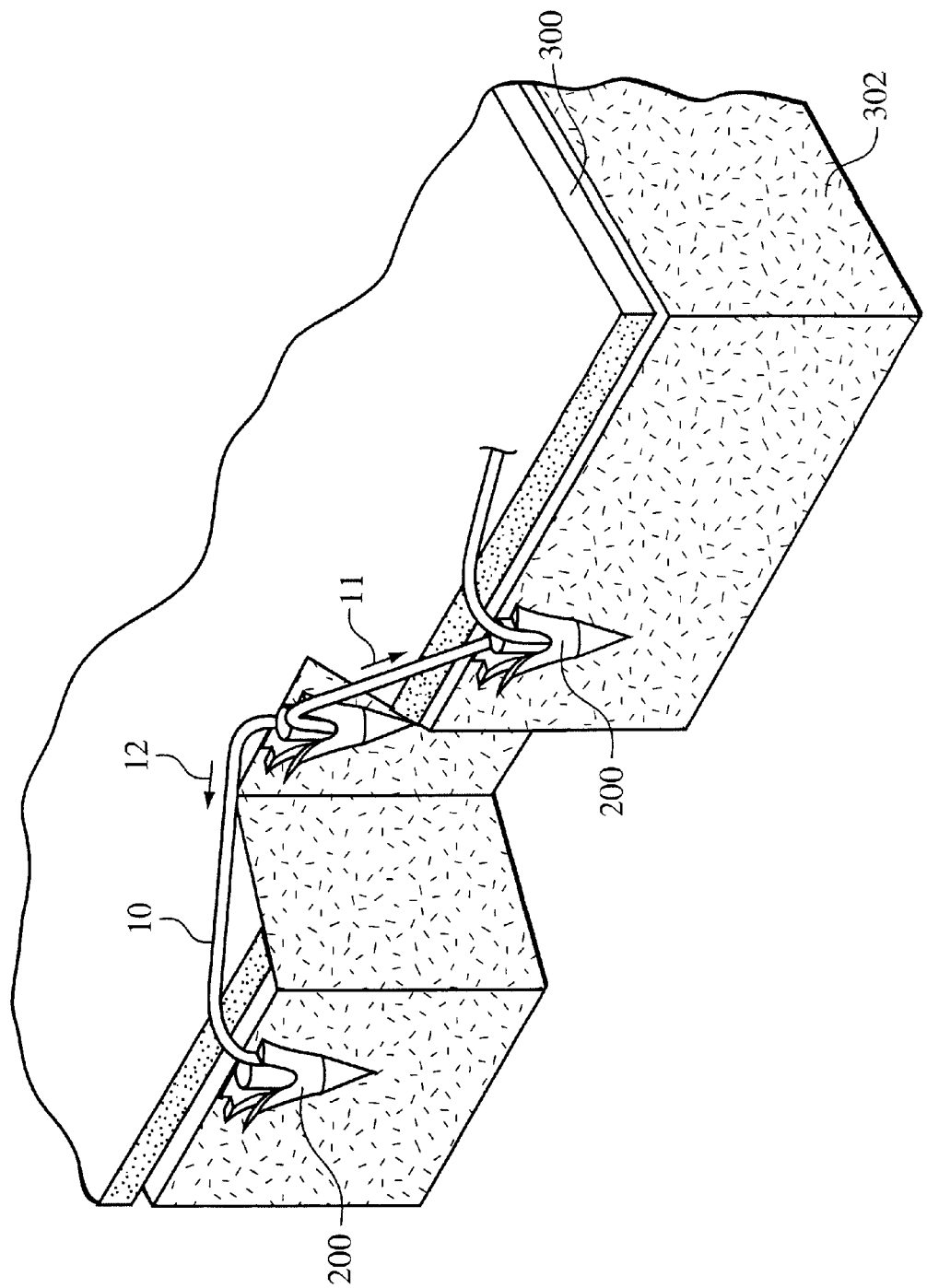
FIG. 6 illustrates the bone anchor of FIG. 4A in use.

Referring to FIG. 6, one or more anchors 200 with suture 10 prethreaded through channel 235 can be deployed through tissue 300 into bone 302. During deployment, wings 219a–219d are initially compressed as they pass through corticol bone, and then expand into the cancellous bone to retain anchors 200 in the bone. By moving suture 10 in the direction of arrow 11, the length of suture between two anchors 200 can be shortened, pulling suture 10 taught, while any tendency of the suture to loosen is limited by movement of suture 10 into proximal restricting portion 239 of channel 235 in response to tension applied to suture 10 in the direction of arrow 12. Suture guiding channel 235 and edges 253a–253d and 254a–254d in anchor 200 thus selectively restricts movement of suture 10 by allowing the passage of suture 10 through portion 237 of channel 235 in a first direction, while restricting subsequent passage of suture 10 in a second, opposite direction by engaging suture 10 in apex 225 at a substantially arbitrary position along the length of the suture 10, without the need for an enlarged portion such as a knot in the suture.

Further alternative embodiments are within the scope of the claims. For example, a single bone anchor can be used, or the suture can be fixed to a first anchor and coupled to a second anchor configured to selectively restrict movement of the suture, as described above. A bone anchor can include only one or more than two cleats. Suture 10 can couple more than two bone anchors in a tissue repair system. Any of a number of different geometries and/or types of bone anchors as described in, e.g., U.S. Pat. No. 5,224,946 to Hayhurst et al., U.S. Pat. No. 5,236,455 to Hayhurst et al., and U.S. Pat. No. 5,100,417 to Cerier et al., the contents of all of which are incorporated herein by reference in their entirety, can be modified to include means according to the invention for selectively restricting passage of suture. Winding posts and side posts can be replaced by any of a number of different structures that contact the suture and retain it in the bone anchor, including eyelets, bosses, etc. Edges can be formed by ridges protruding from the side walls.

What is claimed is:

1. A bone anchor comprising:
    an anchor body configured to be retained within bone, the anchor body defining a path for passage of a member through the anchor body, the anchor body including a restrictor defining an opening having a first portion permitting passage of the member therethrough, and a second portion restricting passage of the member therethrough,
    the restrictor being configured such that movement of the member between the first and second portions is not in a direction of passage of the member along the path through the anchor body.

2. The bone anchor of claim 1 wherein the restrictor includes an edge lining a wall of the opening.

3. The bone anchor of claim 2 wherein the edge is oriented obliquely to a direction of passage of the member through the opening.

4. The bone anchor of claim 2 wherein the restrictor includes multiple edges lining the wall of the opening.

5. The bone anchor of claim 4 wherein at least some of the edges are oriented at the same oblique angle relative to a direction of passage of the member through the opening.

6. The bone anchor of claim 4 wherein at least some of the edges are oriented parallel to each other.

7. The bone anchor of claim 4 wherein the edges are located in the first and second portion.

8. The bone anchor of claim 1 wherein a dimension of the second portion is narrower than a diameter of the member.

9. The bone anchor of claim 1 wherein the opening is triangular in shape.

10. The bone anchor of claim 1 configured such that the member is movable between the first and second portions substantially perpendicularly to a direction of passage of the member through the opening.

11. The bone anchor of claim 1 wherein the anchor body includes a tissue penetrating tip.

12. The bone anchor of claim 1 wherein the anchor body includes a central body member.

13. The bone anchor of claim 12 wherein the central body includes a driver coupling.

14. The bone anchor of claim 1 wherein the anchor body includes a resilient member for engaging bone tissue.

15. The bone anchor of claim 14 wherein the resilient member has a sharp, proximal edge for penetrating bone tissue.

16. The bone anchor of claim 1 wherein the anchor body includes multiple resilient members.

17. The bone anchor of claim 1 wherein the anchor body comprises a unitary body.

18. The bone anchor of claim 1 wherein the restrictor is configured such that moving the member along the path in a first direction causes the member to be moved from the first portion to the second portion.

19. The bone anchor of claim 18 wherein the restrictor is configured such that moving the member along the path in a second direction opposite the first direction causes the member to be moved from the second portion to the first portion.

20. The bone anchor of claim 1 wherein the second portion is proximal to the first portion.

21. The bone anchor of claim 1 wherein the restrictor is configured such that when the member is within the second portion the member is restricted from moving along the path in a first direction.

22. The bone anchor of claim 21 wherein the restrictor is configured such that the member is moved from the second portion to the first portion when the member is moved along the path in a second direction opposite the first direction.

23. The bone anchor of claim 22 wherein the restrictor is configured such that when the member is within the first portion, passage of the member along the path in the second direction is permitted.

24. The bone anchor of claim 1 wherein the restrictor is configured such that movement of the member along the path in a first direction acts to restrict passage of the member along the path, and movement of the member along the path in a second direction acts to permit passage of the member along the path.

25. A tissue repair system comprising:
a first bone anchor including a first anchor body configured to be retained within bone,
a second bone anchor including a second anchor body configured to be retained within bone, and
a flexible member coupling the first and second bone anchors, at least one of the first and second anchor bodies includes a restrictor defining an opening having a first portion for passage of the flexible member therethrough, and a second portion limiting passage of the flexible member therethrough, the flexible member being movable between the first and second portions in a direction non-parallel to a direction of passage of the member through the opening.

26. A bone anchor, comprising:
an anchor body configured to be retained within bone, the anchor body including a restrictor defining an opening for passage of a member therethrough, the restrictor including an edge lining a wall of the opening oriented such that upon movement of the member through the opening in a first direction, the member is also moved non-parallel to the first direction.

27. The bone anchor of claim 26 wherein the edge is oriented such that upon movement of the member through the opening in a second direction opposite the first direction, the member is also moved not along the path.

28. The bone anchor of claim 26 wherein the restrictor includes a second edge lining the wall of the opening.

29. A method comprising:
placing a bone anchor in bone, the bone anchor defining a path for passage of a member through the bone anchor, the bone anchor including a restrictor defining an opening having a first portion for permitting passage of the member therethrough, and a second portion restricting passage of the member therethrough, and
moving the member between the first and second portions not in a direction of passage of the member along the path through the anchor body.

30. The method of claim 29 further comprising engaging the member with an edge lining a wall of the opening.

31. The method of claim 29 wherein moving the member to the second portion comprises moving the member in a direction substantially perpendicular to a direction moved by the member through the first portion.

32. The method of claim 29 further comprising placing a second bone anchor in bone, the second bone anchor being coupled to the first bone anchor by the member.

* * * * *

(12) EX PARTE REEXAMINATION CERTIFICATE (6267th)
United States Patent
Colleran et al.

(10) Number: US 6,656,183 C1
(45) Certificate Issued: Jun. 17, 2008

(54) TISSUE REPAIR SYSTEM

(75) Inventors: Dennis Colleran, North Attleborough, MA (US); Stefan Gabriel, Mattapoisett, MA (US)

(73) Assignee: Smith & Nephew, Inc., Memphis, TN (US)

Reexamination Request:
No. 90/006,989, Apr. 2, 2004

Reexamination Certificate for:
Patent No.: 6,656,183
Issued: Dec. 2, 2003
Appl. No.: 09/986,376
Filed: Nov. 8, 2001

(51) Int. Cl.
*A61B 17/56* (2006.01)

(52) U.S. Cl. .......... 606/72; 606/232
(58) Field of Classification Search .......... 606/62–64, 606/73, 78, 219, 224, 139, 232, 72, 75; 623/13.14, 623/13

See application file for complete search history.

(56) References Cited

U.S. PATENT DOCUMENTS

| | | | |
|---|---|---|---|
| 5,041,129 A | * | 8/1991 | Hayhurst et al. .......... 606/232 |
| 5,123,913 A | * | 6/1992 | Wilk et al. .......... 606/232 |
| 5,258,016 A | | 11/1993 | DiPoto et al. |
| 5,312,438 A | | 5/1994 | Johnson |
| 5,354,298 A | * | 10/1994 | Lee et al. .......... 606/72 |
| 5,383,905 A | | 1/1995 | Golds et al. |
| 5,391,173 A | * | 2/1995 | Wilk .......... 606/144 |
| 5,417,691 A | * | 5/1995 | Hayhurst .......... 606/72 |
| 5,486,197 A | * | 1/1996 | Le et al. .......... 606/232 |
| 5,534,011 A | | 7/1996 | Greene, Jr. et al. |
| 5,571,139 A | | 11/1996 | Jenkins, Jr. |
| 5,573,548 A | | 11/1996 | Nazre et al. |
| 5,702,397 A | | 12/1997 | Goble et al. |
| 5,725,556 A | | 3/1998 | Moser et al. |
| 5,733,307 A | | 3/1998 | Dinsdale |
| 5,782,866 A | * | 7/1998 | Wenstrom, Jr. .......... 606/232 |
| 5,810,848 A | | 9/1998 | Hayhurst |
| 5,810,854 A | * | 9/1998 | Beach .......... 606/151 |
| 5,891,168 A | * | 4/1999 | Thal .......... 606/232 |
| 5,899,920 A | | 5/1999 | DeSatnick et al. |
| 5,964,783 A | | 10/1999 | Grafton et al. |
| 6,027,523 A | * | 2/2000 | Schmieding .......... 606/232 |
| 6,066,160 A | | 5/2000 | Colvin et al. |
| 6,117,162 A | | 9/2000 | Schmieding et al. |
| 6,149,669 A | | 11/2000 | Li |
| 6,159,235 A | | 12/2000 | Kim |
| 6,168,598 B1 | * | 1/2001 | Martello .......... 606/74 |
| 6,200,329 B1 | | 3/2001 | Fung et al. |
| 6,214,031 B1 | | 4/2001 | Schmieding et al. |
| 6,508,830 B2 | | 1/2003 | Steiner |
| 6,517,542 B1 | * | 2/2003 | Papay et al. .......... 606/73 |
| 6,544,281 B2 | | 4/2003 | ElAttrache et al. |
| 6,986,781 B2 | * | 1/2006 | Smith .......... 606/232 |
| 7,037,324 B2 | | 5/2006 | Martinek |

(Continued)

FOREIGN PATENT DOCUMENTS

| | | |
|---|---|---|
| EP | 0 755 656 | 1/1997 |
| WO | WO 9620647 A1 * | 7/1996 |
| WO | WO 01/67962 | 9/2001 |
| WO | WO 03/047437 | 6/2003 |

OTHER PUBLICATIONS

PCT International Search Report, May 4, 2004, 9 pages.
Panalok Anchor with Panacryl Suture, (1997) (2 pages).

*Primary Examiner*—Jimmy G. Foster

(57) ABSTRACT

A bone anchor includes an anchor body configured to be retained within bone. The anchor body includes a restrictor defining an opening having a first portion for permitting passage of a member therethrough, and a second portion restricting passage of the member therethrough. The member is movable between the first and second portions in a direction non-parallel to a direction of passage of the member through the opening. The restrictor includes an edge lining the opening oriented obliquely to a direction of passage of the member through the opening. The anchor body includes one or more resilient members with sharp, proximal edges for penetrating bone tissue.

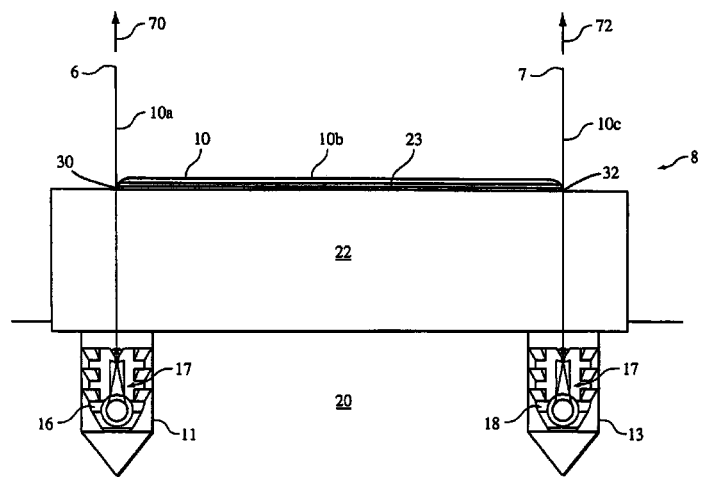

U.S. PATENT DOCUMENTS

| | | |
|---|---|---|
| 2001/0041916 A1 | 11/2001 | Bonutti |
| 2002/0040241 A1 * | 4/2002 | Jarvinen .................. 623/13.14 |
| 2002/0161401 A1 | 10/2002 | Steiner |
| 2003/0065361 A1 | 4/2003 | Dreyfuss |
| 2003/0105489 A1 | 6/2003 | Eichhorn et al. |
| 2003/0120309 A1 * | 6/2003 | Colleran et al. ............. 606/232 |
| 2004/0088004 A1 * | 5/2004 | Rosch ......................... 606/232 |
| 2004/0093031 A1 | 5/2004 | Burkhart et al. |
| 2004/0111117 A1 * | 6/2004 | Colleran et al. ............. 606/232 |

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 9 and 25–32 are cancelled.

Claims 1, 13, 14 and 17 are determined to be patentable as amended.

Claims 2–8, 10–12, 15, 16 and 18–24, dependent on an amended claim, are determined to be patentable.

New claims 33–36 are added and determined to be patentable.

1. A bone anchor comprising:
  an anchor body *having an outwardly extending, bone engaging formation* configured to [be retained] *retain the anchor body* within bone, the anchor body defining a path for passage of a member through the anchor body, the anchor body including a restrictor defining an opening having a first portion permitting passage of the member therethrough, and a second portion restricting passage of the member therethrough, *the second portion including first and second surfaces between which the member is received to compress the member,*
  the restrictor being configured such that movement of the member [between] *from* the first [and second portions] *portion to the second portion to restrict passage of the member through the restrictor* is not [in a direction of passage of the member] along the path through the anchor body *that the member takes to pass through the anchor body,*
  *wherein the opening is triangular in shape.*

13. The bone anchor of claim 12 wherein the central body *member* includes a driver coupling.

14. The bone anchor of claim 1 wherein the [anchor body includes] *bone engaging formation comprises* a resilient member for engaging bone tissue.

17. The bone anchor of claim 1 wherein the anchor body comprises a unitary body *and a resilient member for engaging bone tissue, the resilient member having a sharp, proximal edge for penetrating bone tissue.*

*33. A bone anchor comprising:*
  *an anchor body having an outwardly extending, bone engaging formation configured to retain the anchor body within bone, the anchor body defining a path for passage of a member through the anchor body, the anchor body including a restrictor defining an opening triangular in shape having a first portion permitting passage of the member therethrough, and a second portion restricting passage of the member therethrough, the second portion including first and second surfaces between which the member is received to compress the member,*
  *the restrictor being configured such that movement of the member between the first and second portions is not in a direction of passage of the member along the path through the anchor body.*

*34. The bone anchor of claim 33 configured such that the member is movable between the first and second portions substantially perpendicularly to a direction of passage of the member through the opening.*

*35. The bone anchor of claim 33 wherein the restrictor is configured such that moving the member along the path in a first direction causes the member to be moved from the first portion to the second portion.*

*36. The bone anchor of claim 35 wherein the restrictor is configured such that moving the member along the path in a second direction opposite the first direction causes the member to be moved from the second portion to the first portion.*

* * * * *